United States Patent [19]

Burke et al.

[11] Patent Number: 4,618,578

[45] Date of Patent: Oct. 21, 1986

[54] EXPRESSION OF GLYCOPROTEIN D OF HERPES SIMPLEX VIRUS

[75] Inventors: Rae L. Burke; Mickey S. Urdea; Pablo D. T. Valenzuela, all of San Francisco, Calif.

[73] Assignee: Chiron Corporation, Emeryville, Calif.

[21] Appl. No.: 631,669

[22] Filed: Jul. 17, 1984

[51] Int. Cl.[4] ...................... C12P 21/00; C12N 15/00; C12N 1/00; C07H 21/04

[52] U.S. Cl. .................................. 435/68; 435/172.3; 435/317; 536/27; 935/27; 935/28; 935/12

[58] Field of Search ...................... 435/172.3, 68, 317, 435/255, 253; 260/112 R, 112.5 R; 536/27-29; 935/27, 28, 12

[56] References Cited

U.S. PATENT DOCUMENTS

| | | | |
|---|---|---|---|
| 4,317,811 | 3/1982 | Bertland et al. | 424/89 |
| 4,374,127 | 2/1983 | Larson et al. | 424/89 |

OTHER PUBLICATIONS

J. Hilfenhaus et al., (1981) 17th Intl. Cong. Herpes Virus of Man and Animal, 52:321-331.
Watson et al., (1982) Science, 218:381-382.
Roizman et al., (1982) Devel. Biol. Standard, 52:287-304.
Nahmias et al., (1979) Disease-a-Month, 25:5-49.
Berman et al., (1983) Science, 222:524-527.
Weis et al., (1983) Nature, 302:72-74.
Cohen et al., (1984) J. Virol., 49:102-108.
Laskey et al., (1984) Biotechnology, pp. 527-532.

*Primary Examiner*—Blondel Hazel
*Attorney, Agent, or Firm*—Leydig, Voit & Mayer

[57] ABSTRACT

Methods and compositions are provided for the efficient production in yeast of polypeptides which are immunologically cross-reactive with glycoprotein D of the herpes simplex virus. Synthetic DNA fragments encoding for a portion of the glycoprotein, and the naturally-occurring gene encoding for the glycoprotein and portions thereof, are expressed on plasmids in yeast. Secretion may be provided by including a secretory leader and signal processing sequence derived from the α-factor gene. Alternatively, the genes may be expressed intracellularly under the transcriptional control of a promoter derived from a gene in the yeast glycolytic pathway.

*E. coli* strains HB101 containing plasmids pYHS109 and pYHS118 were deposited at the American Type Culture Collection on July 11, 1984, and granted accession nos. 39762 and 39763, respectively.

30 Claims, 3 Drawing Figures

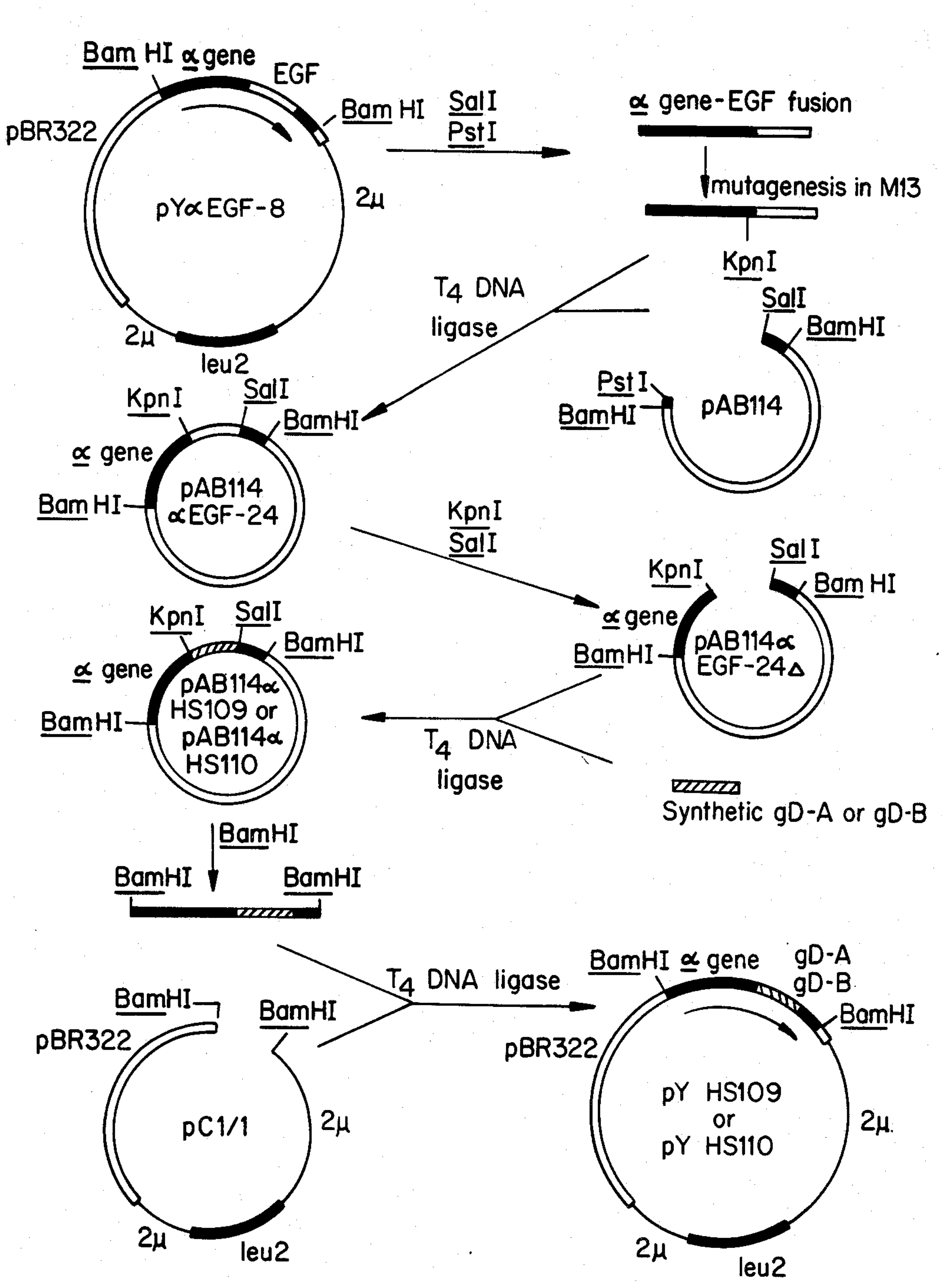
FIG._1.

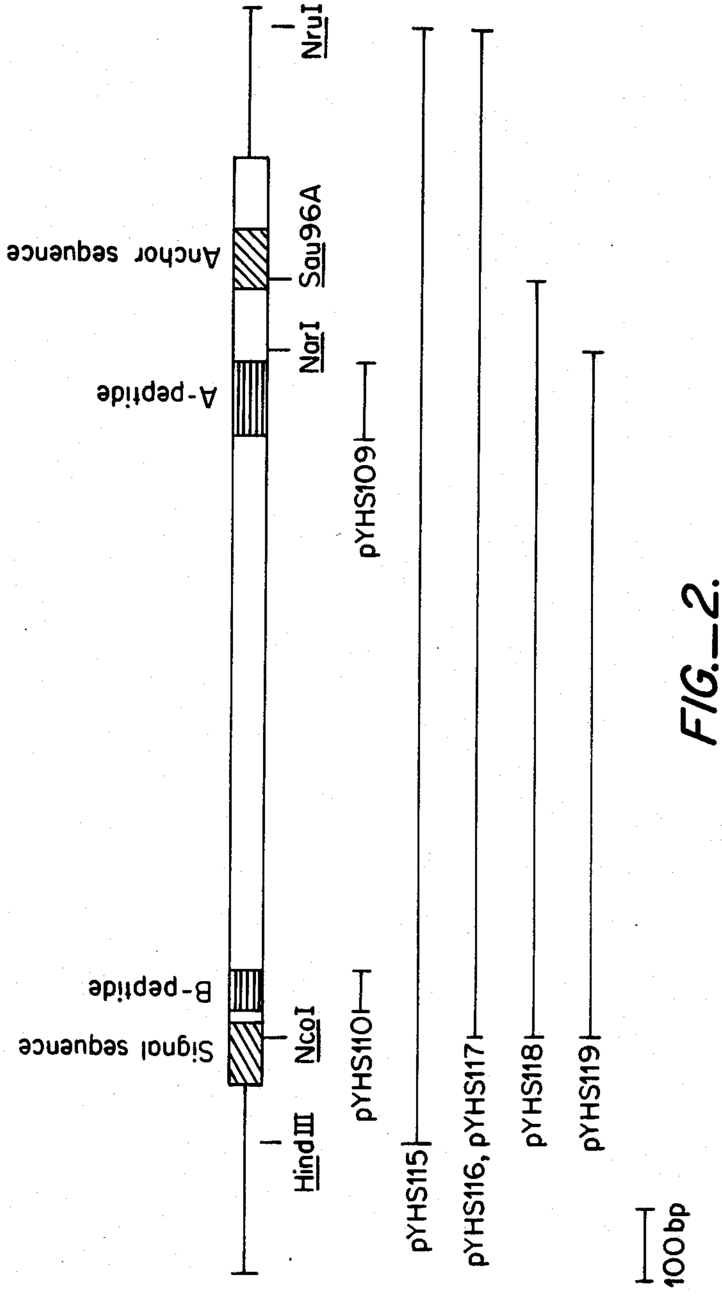
FIG._2.

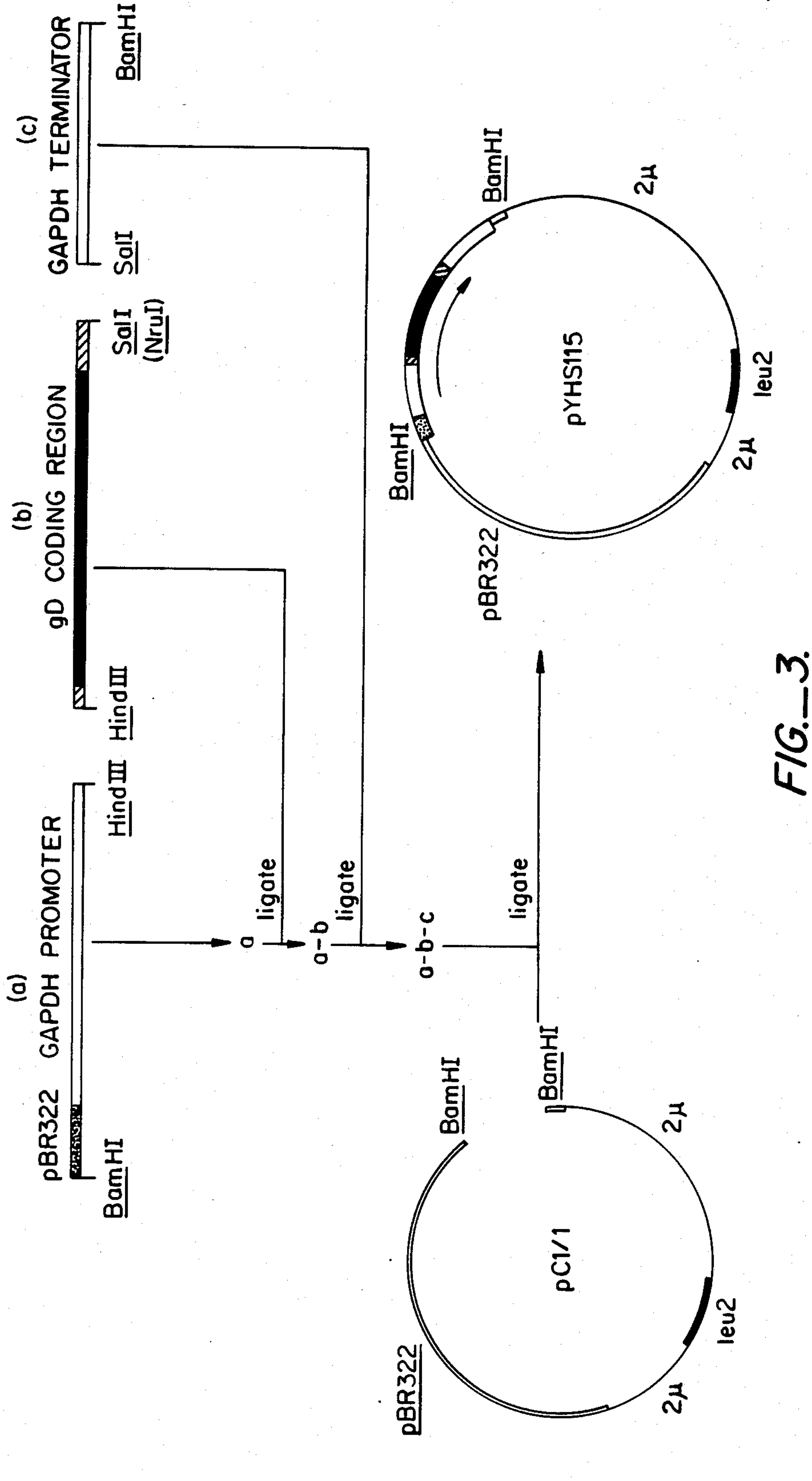
FIG._3.

EXPRESSION OF GLYCOPROTEIN D OF HERPES SIMPLEX VIRUS

BACKGROUND OF THE INVENTION

1. Field of the Invention

The herpesviruses include the herpes simplex viruses, comprising two closely related variants designated types 1 (HSV-1) and 2 (HSV-2). HSV-1 and HSV-2 are responsible for a variety of human diseases, such as skin infections, genital herpes, viral encephalitis, and the like.

The herpes simplex virus is a double stranded DNA virus having a genome of about 150 to 160 kbp packaged within an icosahedral nucleocapsid enveloped in a membrane. The membrane includes a number of virus-specific glycoproteins, the most abundant of which are gB, gC, gD and gE, where gB and gD are cross-reactive between types 1 and 2.

It is a matter of great medical and scientific interest to provide safe and effective vaccines against both HSV-1 and HSV-2. One promising approach has been the use of isolated glycoproteins which have been shown to provide protection when injected into mice subsequently challenged with live virus. One limitation on the use of such "subunit" vaccines, however, has been the difficulty in obtaining sufficient amounts of the glycoproteins. Heretofore, such glycoproteins have been obtained primarily from membranes isolated from a viral culture. The problems associated with large scale culturing of these pathogens and the difficulty in isolating the glycoproteins from the viral genome have substantially precluded the use of glycoprotein vaccines.

It would therefore be desirable to provide a safe and efficient method for the large-scale production of herpes simplex glycoproteins suitable for use as vaccines. In particular, it would be desirable to provide for the production of a polypeptide having an amino acid sequence similar to glycoprotein D, or a portion thereof, which polypeptide can elicit an immune response against both HSV-1 and HSV-2.

2. Description of the Prior Art

Subunit vaccines extracted from chick embryo cells infected with HSV-1 or HSV-2 are described in U.S. Pat. Nos. 4,317,811 and 4,374,127. See also, Hilfenhaus et al. (1982) Develop. Biol. Standard 52: 321–331, where the preparation of a subunit vaccine from a particular HSV-1 strain (BW3) is described. Roizman et al. (1982) Develop. Biol. Standard 52: 287–304, describe the preparation of non-virulent HSV-1×HSV-2 recombinants and deletion mutants which are shown to be effective in immunizing mice. Watson et al. (1982) Science 218: 381–384 describe the cloning and low level expression of the HSV-1 gD gene in *E. coli,* as well as expression of a cloned fragment by injection into the nuclei of frog oocytes. They also present the nucleotide sequence for the gD gene. Weis et al. (1983) Nature 302: 72–74 report higher level expression of gD in *E. coli.* This polypeptide elicits neutralizing antibodies in rabbits. Berman et al. (1983) Science 222: 524–527 report the expression of glycoprotein D in mammalian cell culture. Lasky et al., Biotechnology, June 1984, pp. 527–532 report the use of this glycoprotein D for the immunization of mice. Cohen et al. (1984) J. Virol. 49: 120–108 reports the localization and chemical synthesis of a particular antigenic determinant of gD, contained within residues 8–23 of the mature protein.

SUMMARY OF THE INVENTION

Novel methods and DNA constructs are provided for the production of polypeptides which are immunologically cross-reactive with glycoprotein D (gD) of the herpes simplex virus (HSV). Production of gD in a yeast host provides the advantages of high levels of expression and modification of the polypeptides not available with prokaryotic hosts, without necessitating the use of problematic techniques required for mammalian cell culture. The polypeptide products are useful as vaccines, as reagents for the immunological detection of the virus, for the production of antibodies and monoclonal antibodies, for the detection of antibodies specific for gD, and the like.

The polypeptides produced by the present invention will include at least about nine contiguous amino acids defining an epitopic site found in naturally-occurring glycoprotein D, and may include the entire glycoprotein D sequence. A DNA sequence expressing the desired polypeptide is incorporated in a yeast expression vector, which is used to transform a suitable yeast host. Polypeptides having molecular weights up to about 30 to 50 kilodaltons may include a secretory leader and processing signal sequence providing for secretion of the cleaved polypeptide into the nutrient medium. The polypeptide may then be collected from the nutrient medium without having to lyse the yeast hosts. Alternatively, the polypeptides may be expressed intracellularly, preferably employing a promoter derived from an enzyme in the yeast glycolytic pathway, e.g., glyceraldehyde phosphate dehydrogenase.

BRIEF DESCRIPTION OF THE DRAWINGS

FIG. 1 represents the construction of plasmids pYHS109 and pYHS110 which carry synthetic sequences gD-A and gD-B, respectively, as described in the Experimental section hereinafter.

FIG. 2 is a partial restriction map of the gD region which notes the location of all the gD sequences inserted into yeast expression vectors, as described in the Experimental Section hereinafter.

FIG. 3 represents the construction of plasmid pYHS115 which carries the naturally-occurring gD gene of HSV-1 under the transcriptional control of the GAPDH promoter and terminator, as described in the Experimental section hereinafter.

DESCRIPTION OF THE SPECIFIC EMBODIMENTS

Polypeptides which are immunologically cross-reactive with naturally-occurring glycoprotein D are produced in yeast by recombinant DNA methodology. Production in yeast allows the advantages associated with eukaryotic hosts, e.g., post-translational modification and secretion, without the problems associated with maintaining a mammalian cell culture. The polypeptides of the present invention may be produced from relatively short synthetic DNA fragments encoding for at least about nine amino acids to provide haptens useful for eliciting an immune response specific for gD, e.g., for use in vaccine production. The cloned DNA fragments (or the RNA produced therefrom) may also find use as hybridization probes in a variety of applications. Alternatively, much longer DNA fragments, either synthetic or natural, may be used to produce larger polypeptides for use as vaccines, immunogens, immunological reagents, and the like. The peptides of the present invention will find particular use in the preparation of vaccines against infection by herpes simplex virus.

The glycoprotein D (gD) DNA fragments of the present invention may be of natural or synthetic origins. The natural gD gene of HSV-1 is located on the viral genome between the short internal repeat ($IR_S$) sequence and short terminal repeat ($TR_S$) sequence at the 3'-end thereof. Coding for the mature protein is found on an approximately 1.6 kbp fragment located on a 2.9 kbp SacI restriction fragment of the genome. The entire coding region for the mature protein is located within a HindIII-NruI fragment of the 2.9 kbp SacI fragment. The naturally-occurring gD gene may be employed with or without modification. Regions of the gene may be deleted and/or joined to other DNA fragments as desired. The preparation, cloning and expression of particular fragments of the naturally-occurring gD gene are described in detail in the Experimental section hereinafter.

Synthetic gD sequences will also find use, either alone or in combination with the naturally-occurring sequences. Coding for the synthetic sequences may be based on published nucleotide sequences for gD found in the literature. See, Watson et al. (1982), supra. The synthetic fragments will be sufficiently long to code for at least nine contiguous amino acids with a maximum length equal to that of the naturally-occurring gene or longer. When preparing polypeptides for use as immunological reagents or as vaccines, it is usually desirable that the nucleotide sequence code for an oligopeptide corresponding to an epitopic site of the natural gD protein. Often, such epitopic sites may be predicted by employing the folding rules of Chou and Fasman (1974) Biochemistry 13: 211–222, in conjunction with an analysis of hydrophobic and hydrophilic regions of the protein (Hopp and Woods, 1981, Proc. Natl, Acad. Sci. USA 78: 3824–3828). In particular, it has been found that polypeptides corresponding to amino acids 253–283 and 8–23 in the mature naturally-occurring gD protein will cross-react with antisera raised against the natural gD protein.

A number of techniques are available for synthesizing short single-stranded DNA fragments, e.g., the phosphoramidite method described by Beaucage and Carruthers (1981) Tetrahedron Lett. 22: 1859–1862. Short fragments having a length of about 40 bases or less may be synthesized as a continuous single-stranded fragment. The complementary strand may also be synthesized, and the two strands annealed under appropriate conditions. Alternatively, the complementary strand may be added using DNA polymerase with an appropriate primer sequence.

The synthesis of longer fragments exceeding 100 base pairs is typically accomplished by the preparation of a series of single-stranded DNA fragments including from about 10 to 100 bases, usually from about 15 to 60 bases. The sequences of such fragments are selected so that when the fragments are brought together under annealing conditions, a double stranded fragment having the desired nucleotide sequence is produced. When devising such synthetic nucleotide sequences, the sequences of the individual single stranded DNA fragments are examined to assure that annealing of unmatched segments is avoided. In this way, base pairing occurs only between those segments which are intended to be annealed in the resulting double stranded DNA fragment. Undesired base pairing may usually be avoided by altering one nucleotide (usually the third nucleotide) in preselected ones of the codons.

When preparing synthetic gD DNA fragments, it may sometimes be desirable to modify the reported nucleotide sequence. For example, it will usually be preferred to use codons which are preferentially recognized by the intended yeast host. Specifically, such codons are those which appear at high frequency in the structural genes encoding for the yeast glycolytic enzymes. The nucleotide sequence will usually comprise at least 50% preferred yeast condons, more usually at least 60%, and preferably at least 75%. In some instances, it may be desirable to further alter the nucleotide sequence to create or remove restriction sites or to substitute one or more amino acids in the resulting polypeptide. Such changes may be made to enhance the immunogenicity of the polypeptide, facilitate conjugating the polypeptide to a carrier protein, or the like, etc. It may also be desirable at times to add amino acids to the N-terminus or C-terminus of the polypeptide, where such additional amino acids may provide for a desired result.

The DNA fragments coding for a desired gD fragment will be incorporated in DNA constructs capable of self-replication and expression in yeast. Such DNA constructs will include a replication system recognized by the yeast host, the gD DNA fragment encoding the desired polypeptide product, transcriptional and translational initiation regulatory sequences joined to the 5'-end of the gD sequence, and transcriptional and translational termination regulatory sequences joined to the 3'-end of the gD sequence.

The transcriptional regulatory sequences will include a promoter, which may be the promoter associated with the secretory leader and processing signal sequence. Other promoters may also find use, particularly those involved with the enzymes in a yeast glycolytic pathway, such as the promoters for alcohol dehydrogenase, glyceraldehyde-3-phosphate dehydrogenase (GAPDH), pyruvate kinase, triose phosphate isomerase, phosphoglucoisomerase, phosphofructokinase, and the like. By employing these promoters with other regulatory sequences, such as enhancers, operators, and the like, and using a host having an intact regulatory system, one can regulate the expression of the gD polypeptide product by varying the carbon source, e.g., replacing glucose with galactose; varying the concentration of a nutrient, e.g., phosphate, or changing the temperature with a temperature sensitive promotor or regulatory system.

The transcriptional termination regulatory sequence will include a terminator, preferably a terminator balanced with the promoter to provide for proper transcription. Conveniently, the terminator which is naturally found with the promoter may be employed. The remaining sequences in the construct, including the replication systems for both yeast, e.g., 2μ plasmid, and bacteria, e.g., Col E1, are well known and amply described in the literature.

Enhanced yields of shorter polypeptides may be obtained by employing DNA constructs which include a secretory leader and processing signal sequence to effect secretion and post-translational modification of the gene product in yeast. The upper size limit on the secreted polypeptides is not fixed, although they will usually be below 40 kilodaltons, more usually below about 30 kilodaltons. Moreover, size is not the only determinative criteria as hydrophobic peptides may be more readily secreted than non-hydrophobic peptides. The secretory leader and processing signal sequences will normally be derived from naturally-occurring DNA sequences in yeast which provide for secretion of a polypeptide. Such polypeptides which are naturally secreted by yeast include α-factor, a-factor, acid phosphatase, and the like. If desired, the naturally-occurring sequence may be modified, for example, by reducing the number of lys-arg pairs which define the processing site (while retaining at least one pair), or by reducing the length of the secretory leader sequence (while retaining sufficient length to provide for secretion), or by introducing point mutations, deletions or other modifications which facilitate manipulation, e.g., introducing restriction recognition sites. Conveniently, the secretory leader and processing signal sequence may be joined to the gD DNA fragment by providing appropriate cohesive ends on the gD fragment, by use of appropriate adaptor molecules, or a combination of both.

Polypeptides of the present invention may also be produced intracellularly as follows. After the transformed cell culture has reached a high density, the cells will be separated, typically by centrifugation, lysed, and the gD polypeptides isolated by various techniques, such as extraction, affinity chromatography, electrophoresis, dialysis and combinations thereof.

The polypeptides of the present invention, and fragments thereof, may be employed in a variety of ways. The polypeptides can be employed both as labelled and unlabelled reagents in various immunoassays, bioassays, and the like, for the detection of HSV or antibodies to HSV. Suitable labels include radionuclides, enzymes, fluorescers, chemiluminescers, enzyme substrates or co-factors, enzyme inhibitors, particles, dyes, and the like. Such labelled reagents may be used in a variety of well known assays, such as radioimmunoassays, enzyme immunoassays, e.g., ELISA, fluorescent immunoassays, and the like. See, for example, U.S. Pat. Nos. 3,766,162; 3,791,932; 3,817,837; 3,996,345; and 4,233,402.

Polypeptides of the present invention may also find use in vaccines against herpes. The larger polypeptides, having a molecular weight exceeding about 5,000 daltons, may be used without further modification. The smaller haptens, however, should be conjugated to an appropriate immunogenic carrier in order to elicit the desired immune response. Suitable immunogenic carriers include tetanus toxoid. It will also be possible to link short DNA fragments expressing the gD polypeptides to genes expressing proteins from other pathogenic organisms or viruses. In this way, the resulting fused proteins may provide immunity for more than one disease. In preparing a vaccine, the polypeptides will normally be incorporated in a physiologically acceptable medium, such as water, saline, phosphate buffered saline, and the like. The vaccine may be administered intravenously, intraarterially, subcutaneously, intraperitoneally, or the like. The amount of immunogen employed per dose will be about 5 to 10 μg, if liquid, in a volume of about 0.25 to 1 ml, and may be administered repeatedly at two to four week intervals, usually not more than two to three times.

The following examples are offered by way of illustration and not by way of limitation.

EXPERIMENTAL

All DNA manipulations were done according to standard procedures. See *Molecular Cloning,* T. Maniatis et al., Cold Spring Harbor Lab., 1982. Enzymes used in cloning were obtained either from New England Biolabs or Bethesda Research Laboratories and employed according to the supplier's directions. Yeast were transformed and grown using a variety of media including selective medium (yeast nitrogen base without leucine); YEPD medium, containing 1% (w/v) yeast extract, 2% (w/v) peptone and 2% (w/v) glucose, and others as appropriate and/or detailed below. In the case of plating medium contained 2% (w/v) agar and for transformation 3% top agar.

I. Construction of yeast expression vectors containing synthetic DNA fragments coding for polypeptides A and B of the gD gene.

Nucleotide sequences designated gD-A and gD-B based on portions of the amino acid sequence for glycoprotein D of HSV-1 reported by Watson et al. (1982) Science 218: 381–384, and employing preferred yeast condons, were devised. The gD-A sequence, which encodes amino acids 253–283 (corresponding to amino acids 258–288, as incorrectly numbered by Watson et al., supra.) of the mature protein, was as follows:

```
Processing Site
      ↓
ValProLeuAspLysArgLeuProProGluLeuSerGluThrProAsnAlaThrGln
5'-CCTTGGATAAAAGATTGCCACCAGAATTGTCTGAAACCCCAAACGCTACCCAA
CATGGGAACCTATTTTCTAACGGTGGTCTTAACAGACTTTGGGGTTTGCGATGGGTT

ProGluLeuAlaProGluAspProGluAspSerAlaLeuLeuGluAspProOP OC
CCAGAATTGGCTCCAGAAGACCCAGAAGACTCTGCTTTGTTGGAAGACCCATGATAAG-3'
GGTCTTAACCGAGGTCTTCTGGGTCTTCTGAGACGAAACAACCTTCTGGGTACTATTCAGCT
```

The gD-B sequence, which encodes amino acids 8–23 (corresponding to amino acids 13–28, as incorrectly numbered by Watson et al., supra.) of the mature protein, was as follows:

```
Processing Site
      ↓
ValProLeuAspLysArgSerLeuLysMetAlaAspProAsnArgPheArgGlyLys
5'-CCTTGGATAAAAGATCTTTGAAGATGGCTGACCCAAACAGATTCAGAGGTAAG
CATGGGAACCTATTTTCTAGAAACTTCTACCGACTGGGTTTGTCTAAGTCTCCATTC

AspLeuProOP OC
GACTTGCCATGATAAG-3'
```

-continued

CTGAACGGTACTATTCAGCT

The sequences each include a KpnI cohesive end at the 5′-end and a SalI cohesive end at the 3′-end. Coding for the mature secreted peptide begins after the LysArg processing site. The 5′-end of each sequence is a modification of the 3′-end of the naturally-occurring α-factor secretory leader and processing signal sequence, where the modification consists of a deletion of three glu-ala pairs and a replacement of a leucine by a proline to create a KpnI site in the nucleotide sequence. The 3′-end of each sequence includes two translational stop codons, OP and OC.

Synthetic DNA fragments having the sequences just described were prepared by synthesizing overlapping ssDNA segments as described by Urdea et al. (1984) Proc. Natl. Acad. Sci. USA 80: 7461–7465 using the phosphoramidite method of Beaucage and Caruthers (1981) Tetrahedron Lett. 27: 1859–1862, and annealing and ligating under the following conditions.

The ssDNA fragments were joined as follows: 50 to 100 pmoles of each segment (except the two segments at the 5′-terminii) were 5′-phosphorylated with 5.6 units of T4 polynucleotide kinase (New England Nuclear) in 10 mM dithiothreitol (DDT), 1 mM ATP, 10 mM $MgCl_2$, 100 ng/ml spermidine, 50 mM Tris-HCl, pH 7.8 (total volume: 20 μl) for 30 min at 37° C. Additional T4 kinase (5.6 units) was then added and the reaction continued for 30 min at 37° C. The fragments (except for the 5′ terminii) were combined, diluted to 40 μl with water followed by addition of 60 μl of 1M sodium acetate, 12 μl of 250 mM EDTA, and 5 μg of 1 mg/ml poly-dA. After heating for 5 min at 65° C., the 5′ terminal pieces were added, followed by 420 μl of ethanol (100%). The solution was chilled for 20 min at −80° C., centrifuged, and the pellet was washed twice with ethanol (100%) and dried. The pellet was redissolved in water (18 μl), heated to 100° C. for 2 minutes and then cooled slowly over 1.5 hours to 25° C. in a water bath.

The annealed fragment pool was ligated in a reaction mixture containing T4 DNA ligase (New England Biolabs, 1200 units) 1 mM ATP, 10 mM DTT, 10 mM $MgCl_2$, 100 ng/ml spermidine, and 50 mM Tris-HCl, pH 7.8 (30 μl). After 1 hour at 14° C., the reaction mixture was partially purified by preparative polyacrylamide gel (7%, native) electrophoresis. The DNA was removed from the appropriate gel slice by electroelution and ethanol coprecipitation with poly dA (5 μg).

After assembly, the synthetic gD-A and gD-B fragments were substituted into a KpnI/SalI digested bacterial cloning plasmid pAB114αEGF-24, which plasmid was prepared by cloning a mutagenized fragment of pYEGF-8 into pAB114 (see FIG. 1). The plasmids resulting from the insertion were designated pAB114αHS109 (gD-A) and pAB114αHS110 (gD-B).

The preparation of pAB114 was as follows: Plasmid pAB101 was obtained from the screening of a random yeast genomic library cloned in YEp24 (Fasiolo et al., 1981, J. Biol. Chem. 256: 2324) using a synthetic 20-mer oligonucleotide probe (5′-TTAGTACATTGGTTGGCCGG-3′) homologous to the published α-factor coding region (Kurjan and Herskowitz, Abstracts 1981, Cold Springs Harbor meeting on the Molecular Biology of Yeasts, page 242). Plasmid AB11 was obtained by deleting the HindIII to SalI region of pBR322. An EcoRI fragment of pAB101 carrying the α-factor gene was then inserted into the unique EcoRI site pAB11 to produce pAB112. Plasmid pAB112 was digested to completion with HindIII, and then religated at low (4 μg/ml) DNA concentration to produce plasmid pAB113 in which three 63 bp HindIII fragments were deleted from the α-factor structural gene, leaving only a single copy of mature α-factor coding region. A BamHI site was added to plasmid pAB11 by cleavage with EcoRI, filling in of the overhanging ends by the Klenow fragment of DNA polymerase, ligation of BamHI linkers and religation to obtain a plasmid designated pAB12. Plasmid pAB113 was digested with EcoRI, the overhanging ends filled in, and ligated to BamHI linkers. After digestion with BamHI, the resulting 1500 bp which carries the single copy of the α-factor gene fragment was gel-purified and ligated to pAB12 which had been digested with BamHI and treated with alkaline phosphatase to produce pAB114, which contains a 1500 bp BamHI fragment carrying the α-factor gene.

The preparation of pYEGF-8 was as follows: A synthetic sequence for human epidermal growth factor (EGF) was prepared and ligated to pAB112 (described above) which had been previously completely digested with HindIII and SalI to produce pAB201. The HindIII site lies within the 3′-end of the α-factor gene, and the EGF sequence was inserted using appropriate linkers. The resulting plasmid was designated pAB201.

Plasmid pAB201 (5 μg) was digested to completion with EcoRI and the resulting fragments were filled in with DNA polymerase I Klenow fragment and ligated to an excess of BamHI linkers. The resulting 1.75 kbp fragment was isolated by preparative gel electrophoresis, and approximately 100 ng of this fragment was ligated to 10 ng of yeast plasmid pC1/1 (described below) which had been previously digested to completion with restriction enzyme BamHI and treated with alkaline phosphatase. The ligation mixture of the 1.75 kbp fragment carrying the partial α-factor gene fused to the EGF gene and pC1/1 was used to transform *E. coli* HB101 cells, and transformants were selected based on ampicillin resistance. DNA from one ampicillin resistant clone (designated pYEGF-8) was used to transform yeast AB103 (genotype: MATα. pep 4-3, leu 2-3, lue 2-112, ura 3-52, his 4-580, cir°) cells, and transformants selected based on their $leu^+$ phenotype.

Plasmid pC1/1 is a derivative of pJDB219 (Beggs (1978) Nature 275: 104) where the region derived from bacterial plasmid pMB9 has been replaced by pBR322. The pC1/1 plasmid carries genes for both ampicillin resistance and leucine prototrophy.

Plasmid pAB114αEGF-24 was generated by an in vitro mutagenesis procedure which deleted the sequences coding for the glu-ala processing region in the α-factor leader. Plasmid pAB114αEGF-24 was obtained as follows: a PstI-SalI fragment of pYEGF-8 containing the α-factor leader hEGF fusion was cloned in phage M13 and isolated in single-stranded form. A synthetic 36-mer oligonucleotide primer (5′-GGGGTACCTTTGGATAAAAGAAACTCCGACTCCGAA-3′) was used as a primer for the synthesis of the second strand using the Klenow fragment of DNA polymerase I. After fill-in and ligation at 14° C. for 18 hours, the mixture was treated with $S_1$ nuclease and used to transfect *E. coli* JM101 cells. Phage containing DNA sequences in which the glu-ala region was removed were located using $^{32}P$-labelled primer as a probe. DNA from positive plaques was isolated, digested with PstI and SalI, and the resulting fragment inserted into pAB114 (described above) which has been previously digested to completion with SalI, partially with PstI and treated with alkaline phosphatase. The resulting plasmid was designated pAB114αEGF-24.

Referring again to FIG. 1, the BamHI-BamHI fragment of pAB114αHS109 or pAB114αHS110 (1588 base pairs for gD-A and 1546 base pairs for gD-B) was excised and ligated into the unique BamHI site of pC1/1. The resulting expression vectors were designated pYHS109 for gD-A and pYHS110 for gD-B.

II. Expression of gD-A and gD-B polypeptides.

Plasmids pYHS109 and pYHS110 were both used to transform yeast strain AB103.1 (α, pep 4-3, leu 2-3, leu 2-112, ura 3-52, his 4-580, cir°) to leu prototrophy following the procedure of Hinnen et al. (1978) Proc. Natl. Acad. Sci. USA 75: 1929–1933. The transformants were grown in 1 L cultures at 30° C. in buffered leucine-dificient media to saturation, corresponding to an absorbance of 5 at 650 nm. Yeast cell cultures were maintained at saturation for an additional 12 to 24 hrs with shaking at 30° C. The cultures were then harvested, the intact yeast cells pelleted by centrifugation at 3000 RPM, and the resulting supernatant media filtered through a 0.22μ Millipore filter. This fraction was then passed through a C18 reverse phase column, constructed from 8 Seppak units purchased from Waters. The bound material was eluted with 30 ml of 80% (v/v) acetonitrile, 0.1% (v/v) trifluoroacetic acid in water, evaporated to dryness with a Buchii RotoVap and redissolved in 1.6 ml of distilled water. This material was separated on a HPLC C18 column monitored at 210 nm. The peak corresponding to each respective peptide was collected and its identity confirmed by antigenicity. Each peptide reacted specifically in an ELISA assay using rabbit polyclonal antisera which had been raised against a chemically synthesized gD-B peptide or partial gD-A peptide (residues 256 through 271 of sequence shown in page 9) purchased from Vega Biochemicals. Expression levels, as determined by spectrophotometric measurements of HPLC purified peptides, were on the order of 7.6 mg of gD-A per liter of yeast culture ($OD_{650}=5$) and 0.6 mg of gD-B per liter of yeast culture ($OD_{650}=5$). These results demonstrate the feasibility of expressing a relatively short portion or fragment of a protein and its secretion from yeast cells using an α-factor expression vector.

III. Construction of yeast vectors for high level intracellular expression using fragments of the naturally-occurring gD gene Nucleotide fragments from the naturally-occurring gD gene expressing gD of HSV-1 (gD-1) were also expressed intracellularly in yeast under control of the GAPDH promoter and terminator. A library of EcoRI fragments of HSV-1, strain Patton, cloned into the EcoRI site of pBR322, was made by Dr. Richard Hyman, Hershey Medical Center, Hershey, Pa. The gD is entirely contained with a 2.9 kb SacI fragment within the EcoRI fragment of one clone (clone H) isolated from the HSV-1 library. Clone H was obtained from Dr. Hyman, the 2.9 kb fragment was purified by gel electrophoresis and was used for the construction of several expression vectors which differ in the size of the gD fragment cloned and/or the synthetic linkers used in the 5′ or 3′ ends of the gD fragments. FIG. 2 illustrates the protein coding region (boxed region) and the fragments used for the construction of yeast expression vectors pYHS115, pYHS116, pYHS117, pYHS118 and pYHS119. A description of the construction of each plasmid follows.

1. Construction of pYHS115

Plasmid pYHS115 contains the gD gene in a glyceraldehyde-3-phosphate dehydrogenase (GAPDH) expression cassette cloned into the BamHI site of pC1/1 (described hereinabove).

The GAPDH expression cassette was constructed as follows. Three fragments were prepared (as described in detail below):

(a) A BamHI-HindIII fragment (1407 bp) containing 346 bp of pBR322 and 1061 bp of the GAPDH promoter;

(b) A HindIII-SalI fragment (1430 bp) containing the gD gene, and (c) A SalI-BamHI fragment (900 bp) containing the GAPDH terminator.

These fragments were ligated together and the mixture was digested with BamHI. The 3.7 Kb resulting cassette was isolated by gel electrophoresis and ligated to BamHI cut, alkaline phosphatase-treated pC1/1 (FIG. 3).

Fragment (a) was prepared by completely digesting pGAP347 (described below) with BamHI followed by partial digestion with HindIII. The resulting 1407 bp fragment containing 346 bp of pBR322 and 1061 bp of the GAPDH promoter was isolated by gel electrophoresis.

Construction of pGAP347 was as follows (see co-pending application Ser. No. 468,589, filed Feb. 22, 1983):

PolyA+RNA was isolated from *S. cerevisiae* yeast strain A364A. Double-stranded cDNA was synthesized using AMV reverse transcriptase and *E. coli* DNA polymerase I. Poly-dC-tails were added to the double-stranded cDNA molecule using deoxynucleotide terminal transferase. Poly-dC-tailed cDNA was annealed to poly-dG-tailed pBR322 and used to transform *E. coli* HB101. 1000 transformants were screened by colony hybridization to labeled PolyA+RNA, and a subset further examined by restriction endonuclease mapping, and DNA sequencing. Three clones containing GAPDH sequences were isolated from the pool. One clone (pcGAP-9) contained an insert of about 1200 base pairs and was used for further work.

A yeast gene library was prepared by inserting fragments obtained after partial digestion of total yeast DNA with restriction endonuclease Sau3A in lambda phage Charon 28, according to Blattner et al. (1977) Science 196: 161–169. Several fragments containing yeast GAPDH coding sequences were isolated by screening the phage library with labeled DNA from pcGAP-9. The yeast GAPDH gene of one of these clones was subcloned in pBR322 as a 2.1 kb HindIII fragment (pGAP-1). The GAPDH promoter region was isolated from these clones. A HhaI-HindIII fragment of about 350 bp containing the 3′ portion of the promoter was obtained by: (a) digestion of pGAP-1 with HinfI to generate an approximately 500 bp segment which includes the 3′ part of the promoter and a region encoding the N-terminal amino acids of GAPDH; (b) resection with Bal31 to yield a 400 bp fragment lacking the GAPDH coding region (3′-terminus one base upstream from the ATG initiator codon); (c) addition of HindIII linkers; and (d) cleavage with HhaI. A second HindIII-HhaI fragment of about 700 bp containing the 5′ portion of the promoter was isolated from pGAP-1, ligated to the 350 bp HhaI-HindIII fragment and treated with HindIII. The resulting 1061 bp HindIII fragment was isolated by gel electrophoresis and cloned in HindIII digested, alkaline phosphatase treated pBR322 to produce pGAP347.

Fragment (b) was obtained as follows. Clone H, isolated from the HSV-1 Patton library was digested with SacI. A 2.9 Kb SacI fragment was purified by gel electrophoresis and subsequently digested with HindIII and NruI. The 1430 bp HindIII-NruI fragment containing the gD gene (FIG. 3) was purified by gel electrophoresis, ligated to NruI-SalI adaptors of the following sequence:

```
5'-TGATAAG-3'
   ACTATTCAGCT
```

and digested with SalI.

Fragment (c) was obtained as follows. A 900 bp fragment containing the GAPDH terminator was obtained by BamHI and SalI digestion of pUH28 (described under "Construction of pYHS117") and purification by gel electrophoresis.

2. Construction of pYHS116 pYHS116 contains a gD gene fragment which has a 600 bp deletion at the 5′ end of the coding region that comprises most of the signal sequence coding region. To construct pYHS116, two fragments were obtained:

(a) A BamHI-HindIII fragment (1407 bp) containing 346 bp of pBR322 and 1061 bp of the GAPDH promoter. This fragment was obtained as described under "Construction of pYHS115."

(b) A NcoI-BamHI fragment (2150 bp) containing the partial gD gene followed by the GAPDH terminator. This fragment was obtained by BamHI/NcoI digestion of pYHS115 (described previously) and purification by gel electrophoresis. A HindIII-NcoI chemically synthesized adaptor of the following sequence

```
            metval
5'-AGCTTAACATGGTC-3'
       ATTGTACCAGGTAC
   ↑               ↑
 HindIII          NcoI
```

was ligated to the fragment. This adaptor provides for the first two codons (met and val) fused in the correct reading frame to the partial gD.

Fragments (a) and (b) were ligated together and subsequently digested with BamHI. The resulting 3.5 Kb cassette was isolated by gel electrophoresis and ligated to BamHI cut, alkaline phosphatase treated pC1/1.

3. Construction of pYHS117

Plasmid pYHS117 contains the same partial gD gene clone in pYHS116, fused in reading frame to 7 extra codons at the 5′-end, which code for the first 7 amino acids of the GAPDH structural gene. To construct pYHS117 two fragments were obtained.

(a) An NcoI-SalI digested vector (6.8 Kb) comprising pBR322 sequences, the GAPDH promoter fused to the first 7 codons of the structural gene and the GAPDH terminator. This vector was prepared by NcoI digestion of pUH28 (described below), followed by a partial digestion with SalI and purification by gel electrophoresis.

(b) An NcoI-SalI fragment (1430 bp) containing a partial gD gene. This fragment was obtained by BamHI-SalI digestion of pYHS115 (described previously in Section II.1.) and purification by gel electrophoresis.

These two fragments were ligated together to yield a pBR322 derived vector which contains a partial gD gene fused in reading frame to the 7 first codons of GAPDH gene, flanked by the GAPDH promoter in its 5′ end and by the GAPDH terminator in its 3′ end. The gD expression cassette was obtained by digesting this plasmid with BamHI and purifying a 3.4 Kb fragment by gel electrophoresis. This fragment was ligated to BamHI digested, alkaline phosphatase treated pC1/1 to produce pYHS117.

Plasmid pUH28 contains the coding and 3′ non-coding regions of the hepatitis B surface antigen (HBsAg) gene fused in incorrect reading frame to the first 7 codons of the GAPDH structural gene. This fusion is flanked in its 5′ end by the GAPDH promoter and in its 3′ end by part of the GAPDH coding region followed by the GAPDH terminator. This plasmid was constructed so as to have an NcoI site at the 3′ end of the first 7 codons of the GAPDH gene with the following sequence:

```
            met
5'-AAACAAAATGGTTAGAGTTGCTAATTCC-3'
   TTTGTTTACCAATCTCAACGATTAAGGGTAC
   3'GAPDH      5'GAPDH              NcoI site
   promoter     coding region
```

When this NcoI end is ligated to the partial gD fragment (b, described above) the correct reading frame for the gD protein is regenerated. The SalI site used in the preparation of fragment a (described above) is at the 5′ region of the GAPDH terminator. Therefore, a deletion of the sAg coding plus non-coding regions and GAPDH coding region was obtained by digesting pUH28 with NcoI and partially with SalI.

The construction of pUH28 involves cloning of a fragment that contains the HBsAg coding and 607 bp of 3′ non-coding region prepared from pHBS5-3 Hae2-1 (described below) into the GAPDH containing vector pGAP$_2$′ (described below). To prepare the fragment, pHBS5-3 Hae2-1 was linearized by PstI digestion, partially digested with NcoI and a PstI-NcoI fragment of 1.9 Kb containing pBR322 sequences, HBsAg coding and 3′ sequences was purified by gel electrophoresis. This fragment was subsequently digested with EcoRI and a 1.2 Kb NcoI-EcoRI fragment containing the HBsAg coding and 3′ non-coding regions was purified by gel electrophoresis. Plasmid pGAP$_2$′ was linearized with XbaI and treated with Bal31 to remove approximately 100 bp. The plasmid was subsequently digested with NcoI and a vector fragment of about 9 Kb was purified by gel electrophoresis. The NcoI ends of the vector and the 1.2 Kb NcoI-EcoRI fragment encoding HBsAg were ligated. The recessed end was filled in with Klenow and the resulting blunt end was ligated to the blunt end of the vector obtained by Bal31 digestion to produce pUH28.

pHBS5-3 Hae2-1 is a plasmid that contains the HBsAg coding region and 607 bp of 3′ flanking sequences. This plasmid is a derivative of pHBS5-3 which contains the same insert but only 128 bp of 3′ untranslated region instead of 607 bp. Plasmid pHBS5-3 has been previously described in copending application, Ser. No. 609,540, filed May 11, 1984, (pp. 13–14). pHBS5-3 Hae2-1 was constructed as follows. The HBV genome (3.2 kb) was excised from pHB-3200 (Valenzuela et al., 1979, Nature, 280: 815–819) by restriction digestion with EcoRI. The 3.2 kb fragment was purified by gel electrophoresis and was recircularized by ligation of the EcoRI sticky ends. This closed HBV genome was digested with HaeII, which cuts in the 3′ non-coding region. Recessed ends were filled in with Klenow and HindIII linkers were ligated. The DNA was cut with HindIII and subsequently with XbaI, which has a single site in the HBS coding region. A 1.2 kb XbaI-HindIII fragment containing 586 base pairs of the coding sequence of HBV and 607 base pairs of the 3′ non-coding region was isolated by gel electrophoresis. This fragment was cloned into pHBS5-3 previously cut with XbaI and HindIII and treated with alkaline phosphatase, to yield pHBS5-3 Hae2-1.

pGAP-2 is a pBR322 derived vector which contains a BamHI insert that has the GAPDH coding sequence, 5′ and 3′ flanking regions. There are two XbaI sites in this plasmid: one in the coding region and one in the 3′ flanking sequences. pGAP-2′ is a derivative of pGAP-2 in which the XbaI site present in the 3′ flanking region has been eliminated. For this purpose, 50 μg of pGAP-2 were partially digested with XbaI, treated with Bal31 to remove 25 base pairs per end, and ligated. The plasmids were used to transform *E. coli* HB101 and the transformants were selected for loss of the XbaI site in the 3′ flanking region.

4. Construction of pYHS118

This vector contains a partial gD gene with deletions in two regions: a 600 bp deletion in the 5′-end coding region which comprises most of the signal sequence coding region and a 1300 bp deletion in the 3′-end coding region which includes most of the anchor sequence coding region. It also contains 7 extra codons from the GAPDH gene coding region fused in reading frame at the 5′ end of the gD gene, similar to pYHS117. Plasmid pYHS118 was constructed as follows. pYHS115 was digested with NcoI and SalI, the resulting 1430 bp fragment containing the partial gD was purified by gel electrophoresis and submitted to digestion with NarI (FIG. 2). The two resulting fragments (fragment a: 873 bp containing 5′ end and fragment b: 411 bp containing 3′ end) were independently isolated by gel electrophoresis. Fragment b was subsequently digested with Sau96A to yield three fragments which were separated by gel electrophoresis. The 87 bp Nar-Sau96A fragment was recovered from the gel and was ligated to Sau96I-SalI synthetic adaptors of the following sequence:

```
gly leu ile ala STOP
5'-GGC CTG ATC GCG TAG-3'
       G ACT AGC GCATCAGCT
 ↑                      ↑
Sau96A                 SalI
```

The NarI-(Sau96A)SalI fragment (102 bp) was digested with SalI, purified by gel electrophoresis and ligated with fragment a (previously described). The resulting NcoI-SalI fragment (975 bp) was ligated to NcoI-SalI digested and gel purified pUH28 as described under "Construction of pYHS117." The resulting pBR322 derived vector was digested with BamHI and a 3.1 Kb fragment containing the gD expression cassette was purified by gel electrophoresis. This cassette was ligated to BamHI digested, alkaline phosphatase treated pC1/1 to produce pYHS118.

5. Construction of pYHS119

This vector contains a partial gD gene with deletions in two regions: a 600 bp deletion in the 5′ end coding region which comprises most of the signal sequence coding region and a 2400 bp deletion in the 3′ end coding region which includes all the anchor sequence coding region and about 700 bp upstream of the anchor sequence. It also contains 7 extra codons from the GAPDH gene coding region fused in reading frame at the 5′ end of the gD gene, as pYHS117 and pYHS118. Plasmid pYHS119 was constructed as follows. pYHS115 was digested with NcoI and SalI, the resulting 1430 bp fragment containing the partial gD was purified by gel electrophoresis and subsequently digested with NarI. The 873 bp NcoI-NarI fragment was isolated by gel electrophoresis. A synthetic adaptor of the following sequence:

```
5'-CGCCGCAAATCTAC-3'
     GGCGTTTAGATCAGCT
   ↑               ↑
  NarI            SalI
```

which provides complementary nucleotides to the NarI 5′ overhang, 3 codons in reading frame, a stop codon and a 5′ overhang of SalI, was ligated to the 873 bp NcoI-NarI fragment then digested with SalI. The resulting NcoI-SalI fragment was ligated to pUH28 which has been previously completely digested with NcoI and partially digested with SalI and purified by gel electrophoresis as described under "Construction of pYHS117." The resulting pBR322 derived vector was digested with BamHI and a 2.2 Kb fragment containing the gD expression cassette was purified by gel electrophoresis. This cassette was ligated to BamHI digested, alkaline phosphatase treated pC1/1 to produce pYHS119.

IV. Synthesis of gD from vectors containing partial or complete gD gene

Plasmids pYHS115, 116, 117, 118 and 119 were used to transform yeast strain AB103.1 (α, pep 4-3, leu 2-3, leu 2-113, ura 3-52, his 4-580, cir°) following the procedure of Hinnen et al., (supra.). The transformants were grown to an $OD_{650}=3$ at 30° in YEPD media. The cultures were then harvested by pelleting the yeast cells at 3000 RPM. Cells were spheroplasted with zymolyase and subsequently osmotically lysed in a hypotonic solution. Membranes were spun down in an eppendorf centrifuge, and the pellet was solubilized in 0.1% SDS with protease inhibitors for 16 hours at 4° C. The suspension was centrifuged and total protein, as well as gD specific protein, was determined in both soluble and insoluble fractions. Expression of the gD gene in each of the above described constructions was detected by Western Blot hybridization (Towbin et al., 1979, Proc. Natl. Acad. Sci. USA 76:4350). For this purpose protein samples were submitted to SDS-polyacrylamide gel electrophoresis (Laemmli (1970) Nature 227:680) and electroblotted onto nitrocellulose filters (Towbin et al. supra.). The filter was preincubated with goat serum and subsequently treated with a rabbit polyclonal antibody raised against HSV-1 (Dako). The filter was then incubated with a second goat anti-rabbit antibody conjugated with horseradish peroxidase (Boehringer-Mannheim) and finally it was incubated with horseradish peroxide color development reagent (Bio-Rad) and washed. The results indicate that immunoreactive material is being synthesized in yeast AB103.1 strain transformed with the gD expression vectors, with the exception of transformants containing pYHS115. In all other cases, gD protein corresponds to 0.1 to 0.5% of total yeast cell protein.

According to the present invention, novel DNA constructs are provided for expressing high levels of a polypeptide which is immunologically cross-reactive with herpes simplex virus glycoprotein D. Such expression is carried out in yeast. The genes expressed may be natural, synthetic or a combination of both, and secretion facilitates recovery of the gD gene product. Expression of both short, synthetic fragments corresponding to a portion of the gD protein and long, natural fragments corresponding to the entire gD protein has been demonstrated. Both approaches yield polypeptides that are immunologically reactive with antisera raised against natural gD protein.

Although the foregoing invention has been described in some detail by way of illustration and example for purposes of clarity of understanding, it will be obvious that certain changes and modifications may be practiced within the scope of the appended claims.

What is claimed is:

1. An improved method for producing a polypeptide which is immunologically cross-reactive with glycoprotein D of herpes simplex virus, said method comprising:

growing a yeast host which has been modified to include a DNA sequence expressing a polypeptide of at least nine amino acids defining at least one epitopic site found in naturally-occurring glycoprotein D; and collecting the polypeptide produced by the yeast host.

2. A method as in claim 1, wherein the DNA sequence is under the transcriptional and translational control of regulatory sequences including a secretory leader and processing signal sequence recognized by the yeast host.

3. A method as in claim 1, wherein the DNA sequence is expressed intracellularly.

4. A method as in claim 1, wherein the DNA sequence is under the transcriptional control of a promoter derived from a gene in the yeast glycolytic pathway.

5. A method as in claim 4, wherein the DNA sequence is under the transcriptional control of a promoter derived from a yeast glyceraldehyde phosphate dehydrogenase gene.

6. A method as in claim 1, wherein the yeast host was modified by transformation with a DNA construct capable of self-replication in yeast, said DNA construct carrying the glycoprotein D DNA sequence joined at its 5'-end to transcriptional and translational initiation regulatory sequences and at its 3'-end to transcriptional and translational termination regulatory sequences.

7. A method as in claim 6, wherein the transcriptional and translational initiation regulatory sequences include a secretory leader and processing signal sequence derived from yeast α-factor.

8. A method as in claim 1, wherein the polypeptide encoded by the DNA sequence includes amino acids 8 through 23 of naturally-occurring glycoprotein D.

9. A method as in claim 1, wherein the polypeptide encoded by the DNA sequence includes amino acids 253 through 283 of naturally-occurring glycoprotein D.

10. A method as in claim 1, wherein the DNA sequence is derived from a HindIII-NruI fragment of a glycoprotein D gene of herpes simplex virus type 1.

11. A method as in claim 1, wherein the DNA sequence is derived from a NcoI-NruI fragment of a glycoprotein D gene of herpes simplex virus type 1.

12. A method as in claim 1, wherein the DNA sequence is derived from a NcoI-Sau96A fragment of a glycoprotein D gene of herpes simplex virus type 1.

13. A method as in claim 1, wherein the DNA sequence is derived from a NcoI-NarI fragment of a glycoprotein D gene of herpes simplex virus type 1.

14. A method as in claim 9, wherein the DNA sequence is:

5'-TTGCCACCAGAATTGTCTGAAACC-
CCAAACGCTACCCAA AACGGTGGTCT-
TAACAGACTTTGGGGTTTG-
CGATGGGTT CCAGAATTGGCT-
CCAGAAGACC-
CAGAAGACTCTGCTTTGTTGGAAGACC-
CA-3' GGTCTTAACC-
GAGGTCTTCTGGGTCTTCTGAGAC-
GAAACAACCTTCTGGGT.

15. A method as in claim 8, wherein the DNA sequence is:

5'-TCTTTGAAGATGGCTGACC-
CAAACAGATTCAGAGGTAAGGACTTG-
CCA-" AGAAACTTCTACC-
GACTGGGTTTGTCTAAGTCTCCATTCCT-
GAACGGT.

16. A DNA construct capable of expression in a yeast host of a polypeptide which is immunologically cross-reactive with glycoprotein D of herpes simplex virus, said construct comprising:

a DNA sequence encoding at least nine contiguous amino acids defining at least one epitopic site found in naturally-occurring glycoprotein D;

transcriptional and translational initiation regulatory sequences joined to the 5'-end of the DNA sequence, which initiation sequences are recognized by yeast;

transcriptional and translational termination regulatory sequences joined to the 3'-end of the DNA sequence, which termination sequences are recognized by yeast; and a yeast replication system.

17. A DNA construct as in claim 16, wherein regulatory sequences include a secretory leader and processing signal sequence.

18. A DNA construct as in claim 16, wherein the transcriptional initiation sequences include a promoter derived from a gene in the yeast glycolytic pathway.

19. A DNA construct as in claim 18, wherein the promoter is derived from a yeast glyceraldehyde phosphate dehydrogenase gene.

20. A DNA construct as in claim 16, wherein the DNA sequence is a synthetic fragment encoding an epitope that is cross-reactive between types 1 and 2 of glycoprotein D.

21. A DNA construct as in claim 20, wherein the epitope will elicit neutralizing antibodies to both types 1 and 2.

22. A DNA construct as in claim 21, wherein the DNA sequence encodes for at least nine amino acids occupying positions 8 through 23 of naturally-occurring glycoprotein D, employing preferred yeast codons.

23. A DNA construct as in claim 21, wherein the DNA sequence encodes for at least nine amino acids occupying positions 253 through 283 of naturally-occurring glycoprotein D, employing preferred yeast codons.

24. A DNA construct as in claim 16, wherein the DNA sequence is derived from a NcoI-NruI fragment of a glycoprotein D gene of herpes simplex virus type 1.

25. A DNA construct as in claim 16, wherein the DNA sequence is derived from a NcoI-Sau96A fragment of a glycoprotein D gene of herpes simplex virus type 1.

26. A DNA construct as in claim 16, wherein the DNA sequence is derived from a HindIII-NruI fragment of a glycoprotein D gene of herpes simplex virus type 1.

27. A DNA construct as in claim 16, wherein the DNA sequence is derived from a NcoI-NarI fragment of a glycoprotein D gene of herpes simplex virus type 1.

28. A DNA construct as in claim 22, wherein the DNA sequence is:

5'-TCTTTGAAGATGGCTGACC-
CAAACAGATTCAGAGGTAAGGACTTG-
CCA-3' AGAAACTTCTACC-
GACTGGGTTTGTCTAAGTCTCCATTCCT-
GAACGGT.

29. A DNA construct as in claim 23, wherein the DNA sequence is:

5'-TTGCCACCAGAATTGTCTGAAACC-
CCAAACGCTACCCAA AACGGTGGTCT-
TAACAGACTTTGGGGTTTG-
CGATGGGTT CCAGAATTGGCT-
CCAGAAGACC-
CAGAAGACTCTGCTTTGTTGGAAGACC-
CA-3' GGTCTTAACC-
GAGGTCTTCTGGGTCTTCTGAGAC-
GAAACAACCTTCTGGGT.

30. A plasmid selected from the group consisting of pHS109, pHS110, pYHS115, pYHS116, pYHS117, pYHS118, and pYHS119.

* * * * *